US00PP16882P2

(12) United States Plant Patent
Kobayashi

(10) Patent No.: US PP16,882 P2
(45) Date of Patent: Jul. 25, 2006

(54) POINSETTIA PLANT NAMED 'PER975'

(50) Latin Name: *Euphorbia pulcherrima*
Varietal Denomination: PER975

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/151,829

(22) Filed: Jun. 14, 2005

(51) Int. Cl.
*A01H 5/00* (2006.01)

(52) U.S. Cl. ..... Plt./303

(58) Field of Classification Search ..... Plt./303
See application file for complete search history.

*Primary Examiner*—Kent Bell
(74) *Attorney, Agent, or Firm*—C. A. Whealy

(57) ABSTRACT

A new and distinct cultivar of Poinsettia plant named 'PER975', characterized by its uniform, upright and mounded plant habit; vigorous growth habit; medium green-colored leaves; inflorescences with pink to pale yellow-colored flower bracts; early-season flowering; large cyathia clusters; and excellent post-production longevity.

1 Drawing Sheet

Botanical designation: *Euphorbia pulcherrima* Willd.
Cultivar denomination: 'PER975'.

BACKGROUND OF THE INVENTION

The present Invention relates to a new and distinct cultivar of Poinsettia plant, botanically known as *Euphorbia pulcherrima* Willd., and hereinafter referred to by the name 'PER975'.

The new Poinsettia a product of a planned breeding program conducted by the Inventor in Encinitas, Calif. The objective of the breeding program is to create new early flowering Poinsettia cultivars having strong stems, recurved leaves and flower bracts, attractive flower bract coloration, uniform plant habit and excellent post-production longevity.

The new Poinsettia originated from a cross-pollination made by the Inventor in December, 1997, of a proprietary selection of *Euphorbia pulcherrima* Willd. identified as code number R-03, not patented, as the female, or seed, parent, with a proprietary selection of *Euphorbia pulcherrima* Willd. identified as R-07, not patented, as the male, or pollen, parent. The cultivar PER975 was discovered and selected by the Inventor as a flowering plant within the progeny of the stated cross-pollination in a controlled environment in Encinitas, Calif., in November, 1998.

Asexual reproduction of the new Poinsettia by terminal cuttings propagated in a controlled environment in Encinitas, Calif., since January, 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'PER975'. These characteristics in combination distinguish 'PER975' as a new and distinct cultivar:

1. Uniform, upright and mounded plant habit.
2. Vigorous growth habit.
3. Medium green-colored leaves.

4. Inflorescences with pink to pale yellow-colored flower bracts.
5. Early-season flowering; natural season flower maturity date is late November for plants grown in Encinitas, Calif.
6. Large cyathia clusters.
7. Excellent post-production longevity.

Plants of the new Poinsettia differ from plants of the female parent selection primarily in flower bract color as plants of the female parent selection have pink-colored flower bracts.

Plants of the new Poinsettia differ from plants of the male parent selection primarily in flower bract color as plants of the male parent selection have pink-colored flower bracts. In addition, plants of the new Poinsettia have smooth leaves and flower bracts whereas plants of the male parent selection have slightly reflexed leaves and flower bracts.

Plants of the new Poinsettia can be compared to plants of the cultivar Amazone, disclosed in U.S. Plant Pat. No. 12,604. In side-by-side comparisons conducted in Encinitas, Calif., plants of the new Poinsettia differed from plants of the cultivar Amazone in the following characteristics:

1. Plants of the new Poinsettia were more vigorous than plants of the cultivar Amazone.
2. Leaf margins of plants of the new Poinsettia were typically lobed whereas leaf margins of plants of the cultivar Amazone were typically entire.
3. Plants of the new Poinsettia flowered about nine days earlier than plants of the cultivar Amazone.
4. Plants of the new Poinsettia and the cultivar Amazone differed in flower bract coloration.

Plants of the new Poinsettia can be compared to plants of the cultivar 3-91, disclosed in U.S. Plant Pat. No. 9,602. In side-by-side comparisons conducted in Encinitas, Calif., plants of the new Poinsettia differed from plants of the cultivar 3-91 in the following characteristics:

1. Plants of the new Poinsettia flowered about two weeks earlier than plants of the cultivar 3-91.
2. Plants of the new Poinsettia and the cultivar 3-91 differed in flower bract coloration.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the bottom of the sheet comprises a side perspective view of a typical flowering plant of 'PER975' grown in a container.

The photograph at the top of the sheet is a close-up view of typical inflorescences of 'PER975'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures averaging about 24° C., night temperatures averaging about 19° C. and light levels about 4,000 foot-candles. Single plants were grown in 16.5 -cm pots and pinched once. Plants were flowered under natural season short day/long night conditions. Plants were about 21 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphrbia pulcherrima* Willd. cultivar PER975.

Parentage:

*Female parent*.—Proprietary selection of *Euphorbia pulcherrima* Willd. identified as code number R-03, not patented.

*Male parent*.—Proprietary selection of *Euphorbia pulcherrima* Willd. identified as code number R-07, not patented.

Propagation:

*Type cutting*.—Terminal cuttings.

*Time to initiate roots*.—About 10 days at 20 to 22° C.

*Time to develop roots*.—About four weeks at 20 to 22° C.

*Root description*.—Thick, fibrous; white in color.

*Rooting habit*.—Freely branching.

Plant description:

*Growth habit*.—Upright, uniform and mounded plant habit; inverted triangle. Vigorous growth habit.

*Plant height*.—About 41 cm.

*Plant diameter or spread*.—About 57 cm.

*Lateral branch description*.—Quantity: About eight lateral branches develop after pinching. Length: About 38 cm. Diameter: About 5 mm. Internode length: About 3.5 cm. Strength: Strong. Texture: Smooth; glabrous. Color: 144B.

*Foliage description*.—Arrangement: Alternate, single. Length: About 14 cm. Width: About 11.6 cm. Shape: Elliptic. Apex: Acuminate. Base: Acute. Margin: Entire with irregular lobing. Venation pattern: Pinnate. Texture, upper surface: Glabrous, smooth. Texture, lower surface: Slightly pubescent. Color: Developing and fully expanded foliage, upper surface: 147A. Developing and fully expanded foliage, lower surface: 147B. Venation, upper surface: 147B. Venation, lower surface: 147C. Petiole: Length: About 6.3 cm. Diameter: About 3 mm. Texture, upper and lower surfaces: Smooth; glabrous. Color, upper and lower surfaces: 144C.

Inflorescence description:

*Inflorescence type and habit*.—Inflorescences are compound corymbs of cyathia with colored flower bracts subtending the cyathia. One inflorescence per lateral branch. Flowers are not fragrant. Flowers persistent.

*Natural flowering season*.—Autumn/winter in Northern Hemisphere. Flower initiation and development is induced under long nyctoperiod conditions. Early season flowering, response time, about 8 weeks; natural season flower maturity date is late November for plants grown in Encinitas, Calif.

*Post-production longevity*.—Plants of the new Poinsettia maintain good substance and bract color for about four weeks under interior conditions.

*Inflorescence size*.—Diameter: About 30 cm. Height (depth): About 8 cm.

*Flower bracts*.—Quantity per inflorescence: About 22. Length, largest bracts: About 13.5 cm. Width, largest bracts: About 11.5 cm. Shape: Elliptic. Apex: Acuminate. Base: Acute to attenuate. Margin: Entire with occasional lobing. Texture, upper and lower surfaces: Glabrous; velvety. Surface, upper and lower surfaces: Slightly rugose. Aspect: Mostly flat. Venation pattern: Pinnate. Color: Developing and transitional bracts, upper surface: 4D finely speckled with 37C to 37D. Developing and transitional bracts, lower surface: 36C to 36D. Fully expanded bracts, upper surface: 4D finely speckled with 38B to 38C and occasional flecks of 38A; color becoming closer to 12D with development. Fully expanded bracts, lower surface: 38B to 38C. Venation, upper and lower surfaces: Similar to flower bract color. Bract petiole: Length: About 1.5 cm. Diameter: About 3 mm. Texture, upper and lower surfaces: Smooth; glabrous. Color, upper and lower surfaces: 145B.

*Cyathia*.—Quantity per corymb: About ten to twelve. Diameter of cyathia cluster: About 4 cm by 4.5 cm. Length: About 1.2 cm. Width: About 8 mm. Shape: Ovoid. Color, immature: 145A. Color, mature: 145A to 145B. Nectaries: Quantity per cyathium: About one or two. Size: About 3 mm by 6 mm. Color: 13C. Peduncle: Length: About 2.5 cm. Diameter: About 2 mm. Strength: Strong. Aspect: Mostly upright. Texture: Smooth; glabrous. Color: 145B. Stamens: Quantity per cyathium: About ten. Anther shape: Bi-lobed. Anther length: About 1 mm. Anther color: 11A. Amount of pollen: Scarce. Pollen color: 12A. Pistils: None observed.

Disease/pest resistance: Resistance of pathogens and pests common to Poinsettias has not been observed on plants grown under commercial conditions.

It is claimed:

1. A new and distinct cultivar of Poinsettia plant named 'PER975', as illustrated and described.

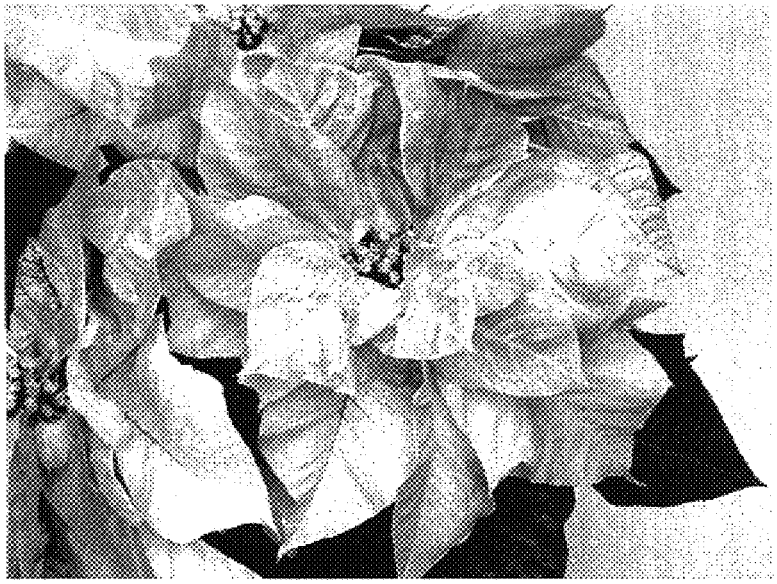
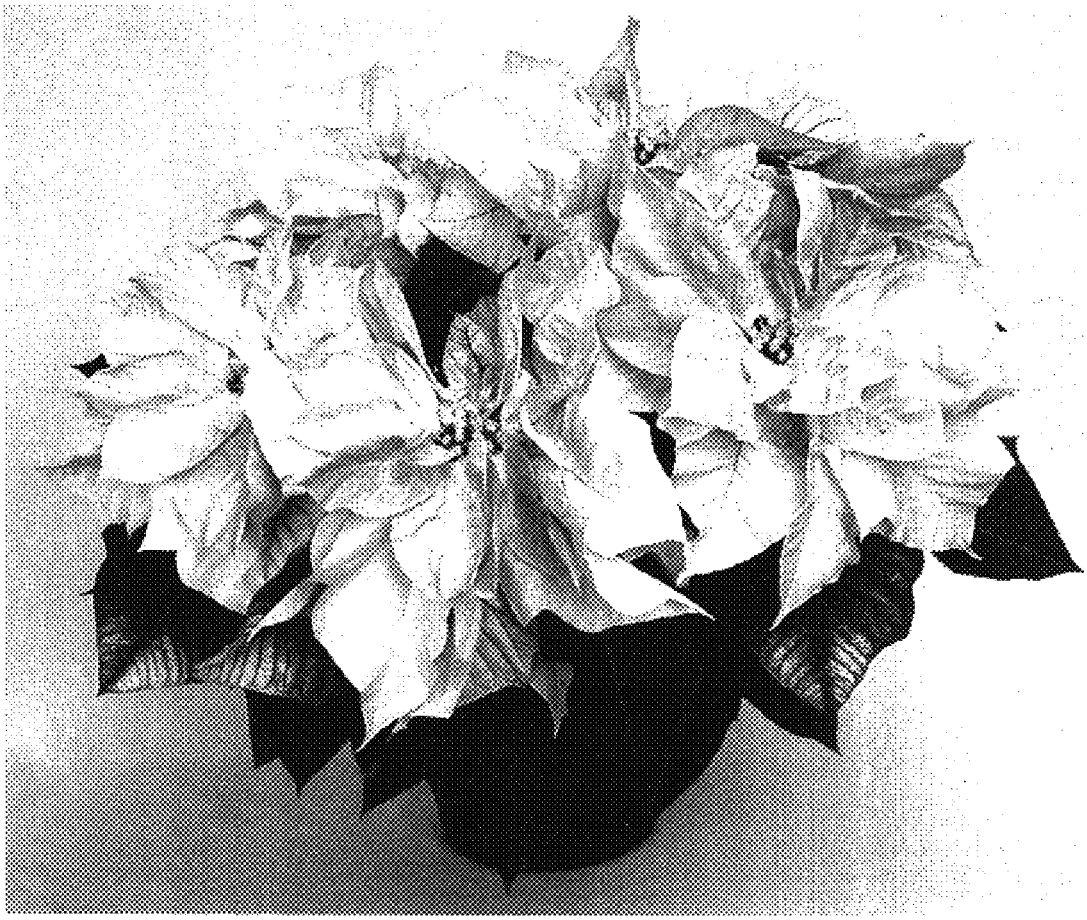

* * * * *